US012734174B2

(12) United States Patent
Alam

(10) Patent No.: US 12,734,174 B2
(45) **Date of Patent: *Sep. 15, 2026**

(54) TREATMENT OF A SELECTIVE POPULATION OF PATIENTS HAVING DEMENTIA WITH LEWY BODIES

(71) Applicant: EIP Pharma, LLC, Boston, MA (US)

(72) Inventor: John Jahangir Alam, Boston, MA (US)

(73) Assignee: EIP Pharma, LLC, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/312,779

(22) Filed: Aug. 28, 2025

(65) Prior Publication Data

US 2025/0387399 A1 Dec. 25, 2025

Related U.S. Application Data

(63) Continuation of application No. 18/707,318, filed as application No. PCT/US2022/049052 on Nov. 4, 2022.

(60) Provisional application No. 63/276,529, filed on Nov. 5, 2021.

(51) Int. Cl.

*A61K 31/5025* (2006.01)
*A61K 31/519* (2006.01)
*A61P 25/14* (2006.01)
*A61P 25/28* (2006.01)

(52) U.S. Cl.

CPC ............ *A61K 31/519* (2013.01); *A61P 25/14* (2018.01); *A61P 25/28* (2018.01)

(58) Field of Classification Search

CPC ....... A61K 31/5025; A81P 25/28; A61P 25/28
USPC .......................................................... 514/248
See application file for complete search history.

(56) References Cited

U.S. PATENT DOCUMENTS

| | | | |
|---|---|---|---|
| 7,956,198 | B2 | 6/2011 | Sattigeri et al. |
| 8,304,413 | B2 | 11/2012 | Kossen et al. |
| 8,338,412 | B2 | 12/2012 | Bemis et al. |
| 8,697,627 | B2 | 4/2014 | Alam |
| 9,427,438 | B2 | 8/2016 | Alam |
| 9,427,439 | B1 | 8/2016 | Alam |
| 9,539,259 | B2 | 1/2017 | Zack et al. |
| 9,579,322 | B2 | 2/2017 | Alam |
| 10,420,770 | B2 | 9/2019 | Alam |
| 10,653,695 | B2 | 5/2020 | Alam et al. |
| 11,466,008 | B2 | 10/2022 | Alam et al. |
| 2003/0135957 | A1 | 7/2003 | Phinney |
| 2004/0204401 | A1 | 10/2004 | Migaly |
| 2005/0004167 | A1 | 1/2005 | Bora et al. |
| 2005/0203111 | A1 | 9/2005 | David |
| 2006/0193920 | A1 | 8/2006 | Bosch et al. |
| 2007/0232632 | A1 | 10/2007 | Lucking et al. |
| 2009/0203702 | A1 | 8/2009 | Bemis |
| 2012/0245188 | A1 | 9/2012 | Huentelman et al. |
| 2012/0289511 | A1 | 11/2012 | Alam |
| 2013/0059798 | A1 | 3/2013 | Bonny |
| 2014/0357638 | A1 | 12/2014 | Alam |
| 2016/0008364 | A1 | 1/2016 | Alam |
| 2016/0030431 | A1 | 2/2016 | Alam |
| 2019/0030035 | A1 | 1/2019 | Alam |
| 2019/0275045 | A1 | 9/2019 | Alam et al. |
| 2019/0381049 | A1 | 12/2019 | Alam |
| 2020/0308176 | A1 | 10/2020 | Alam et al. |
| 2021/0077497 | A1 | 3/2021 | Alam |
| 2022/0133729 | A1 | 5/2022 | Alam |
| 2022/0387432 | A1 | 12/2022 | Alam et al. |
| 2023/0405005 | A1 | 12/2023 | Alam |
| 2025/0339435 | A1 | 11/2025 | Alam |

FOREIGN PATENT DOCUMENTS

| | | | |
|---|---|---|---|
| CN | 1244867 | A | 2/2000 |
| CN | 101103969 | A | 1/2008 |
| CN | 103596951 | A | 2/2014 |
| CN | 103842362 | A | 6/2014 |
| CN | 103842362 | B | 5/2017 |
| CN | 106659723 | A | 5/2017 |
| JP | 2005-526785 | A | 9/2005 |
| JP | 2005-530719 | A | 10/2005 |
| JP | 2007-528393 | A | 10/2007 |
| JP | 2009-541483 | A | 11/2009 |
| JP | 2014-513694 | A | 6/2014 |
| JP | 2017-519807 | A | 7/2017 |
| WO | WO 98/27098 | A1 | 6/1998 |
| WO | WO 03/080024 | A2 | 10/2003 |

(Continued)

OTHER PUBLICATIONS

Adamowicz, D.H. et al.: Hippocampal alpha-synuclein in dementia with Lewy bodies contributes to memory impairment and is consistent with spread of pathology. The Journal of Neurosci., vol. 37, pp. 1675-1684, 2017.*

Fujishiro, H. et al.: Depletion of cholinergic neurons in the nucleus of the medial septum and the vertical limb of the diagonal band in dementia with Lewy bodies. Acta Neuropathol., vol. 111, pp. 109-114, 2006.*

Extended European Search Report mailed Feb. 4, 2020, for Application No. EP 17786786.8.

International Search Report and Written Opinion mailed Jul. 24, 2017, for Application No. PCT/US2017/029012.

International Preliminary Report on Patentability mailed Nov. 1, 2018 for Application No. PCT/US2017/029012.

Extended European Search Report mailed Oct. 27, 2017, for Application No. EP 15819113.0.

International Search Report and Written Opinion mailed Nov. 6, 2015 for Application No. PCT/US2015/039539.

(Continued)

*Primary Examiner* — Charanjit Aulakh

(74) *Attorney, Agent, or Firm* — Wolf, Greenfield & Sacks, P.C.

(57) ABSTRACT

The present invention provides methods and compositions for the treatment of subjects that have Dementia with Lewy Bodies (DLB) but have no substantial tau pathology. Subjects with DLB that have no substantial tau pathology are shown to be particularly responsive to treatment with a selective p38α mitogen activated protein kinase (MAPK) inhibitor compared to subjects with DLB that have substantial tau pathology.

16 Claims, 3 Drawing Sheets

(56) References Cited

FOREIGN PATENT DOCUMENTS

| | | | | |
|---|---|---|---|---|
| WO | WO 03/084524 A1 | 10/2003 | | |
| WO | WO 2005/091891 A2 | 10/2005 | | |
| WO | WO 2008/002465 A2 | 1/2008 | | |
| WO | WO 2012/154814 A1 | 11/2012 | | |
| WO | WO 2014/145485 A2 | 9/2014 | | |
| WO | WO 2016/007616 A1 * | 1/2016 | .......... | A61K 31/519 |
| WO | WO 2017/147601 A1 | 8/2017 | | |
| WO | WO 2017/185073 A1 | 10/2017 | | |
| WO | WO 2019/056003 A1 | 3/2019 | | |
| WO | WO 2019/155464 A1 | 8/2019 | | |
| WO | WO 2019/156991 A1 | 8/2019 | | |
| WO | WO 2020/028810 A1 | 2/2020 | | |
| WO | WO 2020/092107 A1 | 5/2020 | | |
| WO | WO 2020/197399 A1 | 10/2020 | | |
| WO | WO 2021/011432 A1 | 1/2021 | | |

OTHER PUBLICATIONS

International Preliminary Report on Patentability mailed Jan. 19, 2017. for Application No. PCT/US2015/039539.
International Search Report and Written Opinion mailed May 10, 2019 for Application No. PCT/US2019/021930.
International Preliminary Report on Patentability mailed Sep. 24, 2020, for Application No. PCT/US2019/021930.
International Search Report and Written Opinion mailed Dec. 12, 2018, for Application No. PCT/US2018/051558.
International Preliminary Report on Patentability mailed Apr. 2, 2020, for Application No. PCT/US2018/051558.
Extended European Search Report mailed Apr. 29, 2019, for Application No. EP 16860660.6.
International Search Report and Written Opinion mailed Jan. 17, 2017, for Application No. PCT/US2016/058804.
International Preliminary Report on Patentability mailed May 11, 2018, for Application No. PCT/US2016/058804.
Extended European Search Report mailed Apr. 25, 2023 for Application No. 20841310.4.
International Search Report and Written Opinion mailed Oct. 7, 2020, for Application No. PCT/US2020/041736.
International Preliminary Report on Patentability mailed Jan. 27, 2022 for Application No. PCT/US2020/041736.
Extended European Search Report mailed Nov. 6, 2014, for Application No. EP 12782660.0.
Extended European Search Report mailed Sep. 5, 2016, for Application No. EP 16169411.2.
International Search Report and Written Opinion mailed Oct. 16, 2012 for Application No. PCT/US2012/037064.
International Preliminary Report on Patentability mailed Nov. 21, 2013 for Application No. PCT/US2012/037064.
International Search Report and Written Opinion mailed Dec. 15, 2020 for Application No. PCT/US2020/051439.
International Preliminary Report on Patentability mailed Mar. 31, 2022 for Application No. PCT/US2020/051439.
International Search Report and Written Opinion mailed Feb. 7, 2022 for Application No. PCT/US2021/058360.
International Preliminary Report on Patentability mailed May 19, 2023 for Application No. PCT/US2021/058360.
Extended European Search Report for Application No. 21890211.2, mailed Apr. 19, 2024.
International Search Report and Written Opinion mailed Feb. 7, 2022 for Application No. PCT/US2021/058361.
International Preliminary Report on Patentability mailed May 19, 2023 for Application No. PCT/US2021/058361.
Extended European Search Report for Application No. 22890861.2, mailed Aug. 12, 2025.
International Search Report and Written Opinion mailed Feb. 14, 2023 for Application No. PCT/US2022/049052.
International Preliminary Report on Patentability or Application No. PCT/US2022/049052, mailed May 16, 2024.
Adamowicz et al., Hippocampal α-Synuclein in Dementia with Lewy Bodies Contributes to Memory Impairment and Is Consistent with Spread of Pathology. J Neurosci. Feb. 15, 2017;37(7):1675-1684. doi: 10.1523/JNEUROSCI.3047-16.2016. Epub Dec. 30, 2016.
Ahmed et al., New Insights into Cholinergic Neuron Diversity. Front Mol Neurosci. Aug. 27, 2019:12:204. doi: 10.3389/fnmol.2019.00204. eCollection 2019.
Aidem, New Drug for Lewy Body Dementia Shows Promise. Pacific Neuroscience Institute. Oct. 30, 2020. https://www.pacificneuroscienceinstitute.org/blog/clinicaltrials/new-drug-for-lewy-body-dementia-shows-promise [Last accessed Jan. 10, 2022].
Alam et al., Clinical Pharmacology Study of p38 alpha Map Kinase Inhibitor, Neflamapomid (VX-745), in Mild Cognitive Impairment (MCI) Due to Alzheimer's Disease (AD) or Mild AD. J Prev Alz Dis. Dec. 2016;3:277.
Alam et al., LP14- Impact of Alzheimer's Disease (Ad) Related Co-Pathology on Treatment Effects of the Oral P38a Kinase Inhibitor Neflamapimod in Mild-To-Moderate Dementia with Lewy Bodies (Dlb). The Journal of Prevention of Alzheimer's Disease. Nov. 13, 2021; 8(1):S124-S125. 10.14283/jpad.2021.58.
Alam et al., Neflamapimod: Clinical Phase 2b-Ready Oral Small Molecule Inhibitor of p38α to Reverse Synaptic Dysfunction in Early Alzheimer's Disease. J Prev Alzheimers Dis. 2017;4(4):273-278. doi: 10.14283/jpad.2017.41.
Alam, Selective Brain-Targeted Antagonism of p38 MAPKα Reduces Hippocampal IL-1β Levels and Improves Morris Water Maze Performance in Aged Rats. J Alzheimers Dis. 2015;48(1):219-27. doi: 10.3233/JAD-150277.
Alonso et al., Memory formation requires p38MAPK activity in the rat hippocampus. Neuroreport. Oct. 27, 2003;14(15):1989-92. doi: 10.1097/00001756-200310270-00022.
Arevalo-Rodriguez et al., Mini-Mental State Examination (MMSE) for the detection of Alzheimer's disease and other dementias in people with mild cognitive impairment (MCI). Cochrane Database Syst Rev. Mar. 5, 2015;2015(3):CD010783. doi: 10.1002/14651858.CD010783.pub2.
Arvidsson, et al., N-methyl-D-aspartate receptor-mediated increase of neurogenesis in adult rat dentate gyrus following stroke. Eur. J. Neurosci., 2001; 14(1):10-8 [Abstract Only].
Astolfi et al., p38alpha MAPK and Type I Inhibitors: Binding Site Analysis and Use of Target Ensembles in Virtual Screening. Molecules. 2015; 20(9):15842-61.
Azevedo et al., X-ray structure of p38α bound to TAK-715: comparison with three classic inhibitors. Acta Crystallogr. D Biol. Crystallogr. 2012; 68(Pt 8):1041-50.
Bach et al., The Role of CNI-1493 in the Function of Primary Microglia with Respect to Amyloid-β. J Alzheimers Dis. 2011;26(1):69-80. doi: 10.3233/JAD-2011-110179.
Bacher et al., CNI-1493 inhibits Aβ production, plaque formation, and cognitive deterioration in an animal model of Alzheimer's disease. J Exp Med. Jul. 7, 2008;205(7):1593-9. doi: 10.1084/jem.20060467. Epub Jun. 23, 2008.
Bachstetter et al., Attenuation of traumatic brain injury-induced cognitive impairment in mice by targeting increased cytokine levels with a small molecule experimental therapeutic. J Neuroinflammation. Apr. 10, 2015;12:69. doi: 10.1186/s12974-015-0289-5.
Bachstetter et al., Early stage drug treatment that normalizes proinflammatory cytokine production attenuates synaptic dysfunction in a mouse model that exhibits age-dependent progression of Alzheimer's disease-related pathology. J Neurosci. Jul. 25, 2012;32(30):10201-10. doi: 10.1523/JNEUROSCI.1496-12.2012.
Bachstetter et al., The p38α MAPK regulates microglial responsiveness to diffuse traumatic brain injury. J Neurosci. Apr. 3, 2013;33(14):6143-53. doi: 10.1523/JNEUROSCI.5399-12.2013.
Badger et al., Pharmacological profile of SB 203580, a selective inhibitor of cytokine suppressive binding protein/p38 kinase, in animal models of arthritis, bone resorption, endotoxin shock and immune function. J Pharmacol Exp Ther. 1996;279(3):1453-1461.
Bain et al., The selectivity of protein kinase inhibitors: a further update. Biochem J. Dec. 15, 2007;408(3):297-315. doi: 10.1042/BJ20070797.

(56) References Cited

OTHER PUBLICATIONS

Barone et al., SB 239063, a second-generation p38 mitogen-activated protein kinase inhibitor, reduces brain injury and neurological deficits in cerebral focal ischemia. J. Pharmacol. Exp. Ther. 2001; 296(2):312-21.
Barras et al., Drug dosing in obese adults. Aust Prescr. Oct. 2017;40(5):189-193. doi: 10.18773/austprescr.2017.053. Epub Oct. 3, 2017.
Barrientos et al., Aging-related changes in neuroimmune-endocrine function: Implications for hippocampal-dependent cognition, Horm. Behav. 2012;62(3):219-227.
Barrientos et al., Time course of hippocampal IL-1 beta and memory consolidation impairments in aging rats following peripheral infection. Brain Behav Immun. Jan. 2009;23(1):46-54. doi: 10.1016/j.bbi.2008.07.002. Epub Jul. 11, 2008.
Bhaskar et al., Regulation of Tau Pathology by the Microglial Fractalkine Receptor. Neuron. 2010; 68:19-31.
Biglan et al., Safety and Efficacy of Mevidalen in Lewy Body Dementia: A Phase 2, Randomized, Placebo-Controlled Trial. Mov Disord. Mar. 2022;37(3):513-524. doi: 10.1002/mds.28879. Epub Dec. 2, 2021.
Boehm et al., 1-substituted 4-aryl-5-pyridinylimidazoles: a new class of cytokine suppressive drugs with low 5-lipoxygenase and cyclooxygenase inhibitory potency. J Med Chem. 1996;39(20):3929-3937. doi:10.1021/jm9604150.
Boon et al., Non-Amnestic Alzheimer's Disease: A Possible Role for Neuroinflammation?. Alzheimers Dement. Jul. 2017;13(7) Supplement:P1131 (1 page).
Brookmeyer et al., Forecasting the prevalence of preclinical and clinical Alzheimer's disease in the United States. Alzheimers Dement. Feb. 2018;14(2):121-129. doi: 10.1016/j.jalz.2017.10.009. Epub Dec. 7, 2017.
Brown et al., P38 Map kinase inhibitors as potential therapeutics for the treatment of joint degeneration and pain associated with osteoarthritis. J Inflamm (Lond). Dec. 4, 2008;5:22. doi: 10.1186/1476-9255-5-22.
Burgess et al., The human hippocampus and spatial and episodic memory. Neuron. Aug. 15, 2002;35(4):625-41.
Caraccilo et al., Cognitive decline, dietary factors and gut-brain interactions. Mech Ageing Dev. Mar.-Apr. 2014;136-137:59-69. doi: 10.1016/j.mad.2013.11.011. Epub Dec. 12, 2013.
Castello et al., Moving beyond anti-amyloid therapy for the prevention and treatment of Alzheimer's disease. BMC Neurol. Sep. 2, 2014;14:169. doi: 10.1186/s12883-014-0169-0.
Chlan-Fourney et al., The increased density of p38 mitogen-activated protein kinase-immunoreactive microglia in the sensorimotor cortex of aged TgCRND8 mice is associated predominantly with smaller dense-core amyloid plaques. Eur J Neurosci. Apr. 2011;33(8):1433-44. doi: 10.1111/j.1460-9568.2010.07597.x. Epub Feb. 16, 2011.
Chollet, Pharmacologic approaches to cerebral aging and neuroplasticity: insights from the stroke model. Dialogues Clin Neurosci. Mar. 2013;15(1):67-76. doi: 10.31887/DCNS.2013.15.1/fchollet.
Chopra et al., Pharmacological profile of AW-814141, a novel, potent, selective and orally active inhibitor of p38 MAP kinase. Int Immunopharmacol. Apr. 2010;10(4):467-73. doi: 10.1016/j.intimp.2010.01.007. Epub Jan. 20, 2010.
Choudhury et al., Involvement of p38 MAPK in reactive astrogliosis induced by ischemic stroke. Brain Res. 2014; 1551:45-58.
Clark et al., Use of florbetapir-PET for imaging beta-amyloid pathology. JAMA. Jan. 19, 2011;305(3):275-83. doi: 10.1001/jama.2010.2008.
Clarkson et al., Reducing excessive GABA-mediated tonic inhibition promotes functional recovery after stroke. Nature. 2010; 468(7321):305-9.
Colie et al., Neuronal p38α mediates synaptic and cognitive dysfunction in an Alzheimer's mouse model by controlling β-amyloid production. Sci Rep. 2017;7:45306. Published Mar. 31, 2017. doi: 10.1038/srep45306.
Correa et al., The Role of p38 MAPK and Its Substrates in Neuronal Plasticity and Neurodegenerative Disease. J Signal Transduct. 2012;2012:649079. doi: 10.1155/2012/649079. Epub Jun. 25, 2012.
Cortez et al., Aged dominant negative p38α MAPK mice are resistant to age-dependent decline in adult-neurogenesis and context discrimination fear conditioning. Behav Brain Res. 2017;322(Pt B):212-222. doi:10.1016/j.bbr.2016.10.023. Author Manuscript.
Coulthard et al., A broader view of dementia: multiple co-pathologies are the norm. Brain. Jul. 1, 2018;141(7):1894-1897. doi: 10.1093/brain/awy153.
Cummings et al., Defining Disease Modifying Therapy for Alzheimer's Disease. J Prev Alzheimers Dis. 2017;4(2):109-115. doi: 10.14283/jpad.2017.12. Epub Apr. 25, 2017.
Cummings, Challenges to Demonstrating Disease-Modifying Effects in Alzheimer's Disease Clinical Trials. Alzheimers Dement. Oct. 2006;2(4):263-71. doi: 10.1016/j.jalz.2006.07.001.
Davis et al., Comprehensive analysis of kinase inhibitor selectivity. Nat Biotechnol. Oct. 30, 2011;29(11):1046-51. doi: 10.1038/nbt.1990.
Dong et al., Mmp-9, a potential target for cerebral ischemic treatment. Curr Neuropharmacol. Dec. 2009;7(4):269-75. doi: 10.2174/157015909790031157.
Duffy et al., The Discovery of VX-745: A Novel and Selective p38-alpha Kinase Inhibitor. ACS Med Chem Lett. Jul. 28, 2011;2(10):758-63. doi: 10.1021/ml2001455. eCollection Oct. 13, 2011.
Economou et al., Episodic Memory in Alzheimer Disease, Frontotemporal Dementia, and Dementia With Lewy Bodies/Parkinson Disease Dementia: Disentangling Retrieval From Consolidation. Alzheimer Dis Assoc Disord. Jan.-Mar. 2016;30(1):47-52. doi: 10.1097/WAD.0000000000000089.
Edwardson et al., Ischemic stroke prognosis in adults. UpToDate. Official Reprint. 2015. Topic 14086, Version 13.0. 14 pages. <www.uptodate.com>.
Fang et al., Prions activate a p38 MAPK synaptotoxic signaling pathway. PLoS Pathog. Sep. 20, 2018;14(9):e1007283. doi: 10.1371/journal.ppat.1007283. eCollection Sep. 2018.
Fang et al., Synuclein impairs trafficking and signaling of BDNF in a mouse model of Parkinson's disease. Sci Rep. Jun. 20, 2017;7(1):3868. doi: 10.1038/s41598-017-04232-4.
Ferman et al., Dementia with Lewy bodies. Neurol Clin. Aug. 2007;25(3): 741-vii. doi:10.1016/j.ncl.2007.03.001.
Ferraccioli, Current Opinion in anti-inflammatory and immunomodulatory investigational drugs. 2000; 2(1):74-77.
Fiore, Another Drug Moves Amyloid Without Clinical Effects-Study highlights amyloid—Alzheimer's 'disconnect'. MedPage Today. 2015. 4 pages.
Fritz et al., Motor performance differentiates individuals with Lewy body dementia, Parkinson's and Alzheimer's disease. Gait Posture. Oct. 2016:50:1-7. doi: 10.1016/j.gaitpost.2016.08.009. Epub Aug. 11, 2016.
Fujishiro et al., Depletion of cholinergic neurons in the nucleus of the medial septum and the vertical limb of the diagonal band in dementia with Lewy bodies. Acta Neuropathol. Feb. 2006;111(2):109-14. doi: 10.1007/s00401-005-0004-1. Epub Jan. 19, 2006.
Garcia-Alloza et al., Existing plaques and neuritic abnormalities in APP:PSI mice are not affected by administration of the gamma-secretase inhibitor LY-411575. Mol Neurodegener. May 6, 2009;4:19. doi: 10.1186/1750-1326-4-19.
Germann et al., P38 Mapk Signaling—A Robust Therapeutic Target for Rab5-Mediated Neurodegenerative Disease. Int J Mol Sci. Jul. 31, 2020;21(15):5485. doi: 10.3390/ijms21155485.
Giladi et al., Classification of gait disturbances: distinguishing between continuous and episodic changes. Mov Disord. Author manuscript; available in PMC: Sep. 15, 2014. Published in final edited form as: Mov Disord. Sep. 15, 2013;28(11):10.1002/mds.25672. doi: 10.1002/mds.25672.
Gill et al., Differences in rate of functional decline across three dementia types. Alzheimers Dement. Author manuscript; available in PMC Oct. 1, 2014. Published in final edited form as: Alzheimers Dement. Oct. 2013; 9(0): S63-S71. Published online May 2, 2013. doi: 10.1016/j.jalz.2012.10.010.

(56) References Cited

OTHER PUBLICATIONS

Gnanalingham et al., Motor and cognitive function in Lewy body dementia: comparison with Alzheimer's and Parkinson's diseases. J Neurol Neurosurg Psychiatry. Mar. 1997;62(3):243-52. doi: 10.1136/jnnp.62.3.243.
Godl et al., An efficient proteomics method to identify the cellular targets of protein kinase inhibitors. Proc Natl Acad Sci U S A. Dec. 23, 2003;100(26):15434-9. doi: 10.1073/pnas.2535024100. Epub Dec. 10, 2003.
Goldstein et al., Selective p38alpha inhibitors clinically evaluated for the treatment of chronic inflammatory disorders. J Med Chem. Mar. 25, 2010;53(6):2345-53. doi: 10.1021/jm9012906.
Gomperts, Lewy Body Dementias: Dementia With Lewy Bodies and Parkinson Disease Dementia. Continuum (Minneap Minn). Apr. 2016;22(2 Dementia):435-63. doi: 10.1212/CON.0000000000000309.
González-Gutiérrez et al., The Rab5-Rab11 Endosomal Pathway is Required for BDNF-Induced CREB Transcriptional Regulation in Hippocampal Neurons. J Neurosci. Oct. 14, 2020;40(42):8042-8054. doi: 10.1523/JNEUROSCI.2063-19.2020. Epub Sep. 14, 2020.
Graff-Radford, Alzheimer's and dementia: What's the difference? Mayo Clinic. https://www.mayoclinic.org/diseases-conditions/alzheimers-disease/expert-answers/alzheimers-and-dementia-whats-the-difference/faq-20396861. First available at least by Mar. 30, 2019.
Gratwicke et al., Resting state activity and connectivity of the nucleus basalis of Meynert and globus pallidus in Lewy body dementia and Parkinson's disease dementia. Neuroimage. Nov. 1, 2020:221:117184. doi: 10.1016/j.neuroimage.2020.117184. Epub Jul. 22, 2020.
Grupke et al., Understanding history, and not repeating it. Neuroprotection for acute ischemic stroke: from review to preview. Clin. Neurol. Neurosurg. 2015;129:1-9.
Hackam et al., Translation of research evidence from animals to humans. JAMA Oct. 11, 2006;296(14):1731-2. doi: 10.1001/jama.296.14.1731.
Haddad, VX-745 Vertex Pharmaceuticals. Curr Opin Investig Drugs. Aug. 2001;2(8):1070-6.
Hall et al., Plasma Phospho-Tau Identifies Alzheimer's Co-Pathology in Patients with Lewy Body Disease. Mov Disord. Mar. 2021;36(3):767-771. doi: 10.1002/mds.28370. Epub Dec. 7, 2020.
He et al., P38 Mitogen-activated Protein Kinase and Parkinson's Disease. Transl Neurosci. Nov. 12, 2018:9:147-153. doi: 10.1515/tnsci-2018-0022. eCollection 2018.
Hermann et al., Promoting neurological recovery in the post-acute stroke phase: benefits and challenges. Eur Neurol. 2014;72(5-6):317-25. doi: 10.1159/000365171. Epub Oct. 16, 2014.
Herrup, Reimagining Alzheimer's Disease—An Age-Based Hypothesis. J Neurosci. Dec. 15, 2010;30(50):16755-62. doi: 10.1523/JNEUROSCI.4521-10.2010.
Herrup, The case for rejecting the amyloid cascade hypothesis. Nat Neurosci. Jun. 2015;18(6):794-9. doi: 10.1038/nn.4017.
Hideshima et al., Targeting p38 MAPK inhibits multiple myeloma cell growth in the bone marrow milieu. Blood. 2003; 101(2):703-5.
Hoshino et al., Improvement of cognitive function in Alzheimer's disease model mice by genetic and pharmacological inhibition of the EP(4) receptor. J Neurochem. Mar. 2012;120(5):795-805. doi: 10.1111/j.1471-4159.2011.07567.x. Epub Jan. 23, 2012.
Hull et al., Pathways of Inflammatory Activation in Alzheimer's Disease: Potential Targets for Disease Modifying Drugs. Curr Med Chem. Jan. 2002;9(1):83-8. doi: 10.2174/0929867023371292.
Jack Jr et al., Dementia is not synonymous with Alzheimer's disease. Sci Transl Med. Dec. 11, 2019;11(522):eaav0511. doi: 10.1126/scitranslmed.aav0511.
Jackson et al., Physiotherapy is Associated with Improvements in Gait and Balance in Individuals with Cognitive Impairment: A Retrospective Analysis. The Graduate College of The University of Nevada, Las Vegas. May 17, 2019. pp. 1-34.
Jellinger et al., Are dementia with Lewy bodies and Parkinson's disease dementia the same disease? BMC Med. Mar. 6, 2018;16(1):34. doi: 10.1186/s12916-018-1016-8.
Jellinger, Dementia with Lewy bodies and Parkinson's disease-dementia: current concepts and controversies. J Neural Transm (Vienna). Apr. 2018;125(4):615-650. doi: 10.1007/s00702-017-1821-9. Epub Dec. 8, 2017.
Jiang et al., Preclinical and randomized clinical evaluation of the p38α kinase inhibitor neflamapimod for basal forebrain cholinergic degeneration. Nat Commun. 2022;13:1-15. https://doi.org/10.1038/s41467-022-32944-3.
Jordon, Tamoxifen: a most unlikely pioneering medicine. Nat Rev Drug Discov. Mar. 2003;2(3):205-13. doi: 10.1038/nrd1031.
Kalaria et al., Stroke and cognition. Curr Atheroscler Rep 2001;3:334-339. Doi: 10.1007/s11883-001-0028-5.
Karagianni et al., Pharmaceutical Cocrystals: New Solid Phase Modification Approaches for the Formulation of APIs. Pharmaceutics. 2018;10(1):18. Published Jan. 25, 2018. doi:10.3390/pharmaceutics10010018.
Karran et al., The amyloid cascade hypothesis for Alzheimer's disease: an appraisal for the development of therapeutics. Nat Rev Drug Discov. Aug. 19, 2011;10(9):698-712. doi: 10.1038/nrd3505.
Kosaka et al., Lewy body disease and dementia with Lewy bodies. Proc Jpn Acad Ser B Phys Biol Sci. Oct. 10, 2014; 90(8): 301-306. doi: 10.2183/pjab.90.301.
Koschel et al., Implications of dopaminergic medication withdrawal in Parkinson's disease. J Neural Transm (Vienna). Sep. 2022;129(9):1169-1178. doi: 10.1007/s00702-021-02389-x. Epub Jul. 29, 2021.
Kumar et al., p38 MAP kinases: key signalling molecules as therapeutic targets for inflammatory diseases. Nat. Rev. Drug Discov. 2003; 2(9):717-26.
Kummer et al., Non-neuronal cholinergic airway epithelium biology. Curr Opin Pharmacol. Jun. 2014; 16:43-9. doi: 10.1016/j.coph.2014.03.001. Epub Mar. 27, 2014. Abstract only.
Kung et al., Behavioural and Cognitive Changes in Lewy Body Dementias. Behav Neurol. Nov. 11, 2018:2018:2404191. doi: 10.1155/2018/2404191. eCollection 2018.
Lachman et al., Natural History and Outcome in Systemic AA Amyloidosis Abstract Background. N Engl J Med. Jun. 7, 2007;356(23):2361-71. doi: 10.1056/NEJMoa070265.
Lawrence, Alzheimer's will be treated with 'cocktail' of drugs, predicts neuroscientist. The Pharmaceutical Journal. Jan. 2016;296(7885): 2 pages.
Lee et al., Clinical drug development for dementia with Lewy bodies: past and present. Expert Opin Investig Drugs. Nov. 2019;28(11):951-965. doi: 10.1080/13543784.2019.1681398. Epub Oct. 28, 2019.
Lee et al., CX3CR1 Deficiency Alters Microglial Activation and Reduces Beta-Amyloid Deposition in Two Alzheimer's Disease Mouse Models. Am J Pathol. Nov. 2010;177(5):2549-62. doi: 10.2353/ajpath.2010.100265. Epub Sep. 23, 2010.
Li et al., Soluble A-beta oligomers inhibit long-term potentiation through a mechanism involving excessive activation of extrasynaptic NR2B-containing NMDA receptors. J. Neurosci. 2011; 31(18):6627-38.
Liu et al., Nucleus basalis of Meynert revisited: anatomy, history and differential involvement in Alzheimer's and Parkinson's disease. Acta Neuropathol. Apr. 2015;129(4):527-40. doi: 10.1007/s00401-015-1392-5. Epub Jan. 30, 2015.
Lowenberg et al., Specific Inhibition of c-Raf Activity by Semapimod Induces Clinical Remission in Severe Crohn's Disease. J Immunol. Aug. 15, 2005;175(4):2293-300. doi: 10.4049/jimmunol.175.4.2293.
Maphis et al., Selective suppression of the α isoform of p38 MAPK rescues late-stage tau pathology. Alzheimers Res Ther. 2016;8(1):54. Published Dec. 15, 2016. doi:10.1186/s13195-016-0221-y.
Matousek et al., Chronic IL-1β-mediated neuroinflammation mitigates amyloid pathology in a mouse model of Alzheimer's disease without inducing overt neurodegeneration. J. Neuroimmune Pharmacol. 2012; 7(1): 156-164.
Mayer et al., p38 MAP kinase inhibitors: A future therapy for inflammatory diseases. Drug Discovery Today: Therapeutic Strategies. 2006; 3(1):49-54.

(56) References Cited

OTHER PUBLICATIONS

Mcafoose et al., Evidence for cytokine model of cognitive function. Neurosci Biobehav Rev. Mar. 2009;33(3):355-66. doi: 10.1016/j.neubiorev.2008.10.005. Epub Oct. 18, 2008.
Merlini et al., Molecular mechanisms of amyloidosis. N Engl J Med. Aug. 7, 2003;349(6):583-96. doi: 10.1056/NEJMra023144.
Minoshima et al., Metabolic reduction in the posterior cingulate cortex in very early Alzheimer's disease. Ann. Neurol. 1997; 42(1):85-94.
Molloy et al., The role of levodopa in the management of dementia with Lewy bodies. J Neurol Neurosurg Psychiatry. Sep. 2005;76(9):1200-3. doi: 10.1136/jnnp.2004.052332.
Montalban et al., KR-003048, a potent, orally active inhibitor of p38 mitogen-activated protein kinase. Eur J Pharmacol. 2010;632(1-3):93-102. doi:10.1016/j.ejphar.2010.01.011.
Morato et al., Symptomatic and Disease-Modifying Therapy Pipeline for Alzheimer's Disease: Towards a Personalized Polypharmacology Patient-Centered Approach. Int J Mol Sci. Aug. 18, 2022;23(16):9305. doi: 10.3390/ijms23169305.
Morris et al., Inconsistencies and controversies surrounding the amyloid hypothesis of Alzheimer's disease. Acta Neuropathol Commun. Sep. 18, 2014;2:135. doi: 10.1186/s40478-014-0135-5.
Morris et al., Overview of the cholinergic contribution to gait, balance and falls in Parkinson's disease. Parkinsonism Relat Disord. Jun. 2019:63:20-30. doi: 10.1016/j.parkreldis.2019.02.017. Epub Feb. 14, 2019.
Morris et al., Overview of the Cholinergic Contribution to Gait, Balance and Falls in Parkinson's Disease. Parkinsonism Relat Disord. Author manuscript; available in PMC: Jun. 1, 2020. Published in final edited form as: Parkinsonism Relat Disord. Feb. 14, 2019;63:20-30. doi: 10.1016/j.parkreldis.2019.02.017.
Mrak et al., Common inflammatory mechanisms in Lewy body disease and Alzheimer disease. J Neuropathol Exp Neurol. Aug. 2007;66(8):683-6. doi: 10.1097/nen.0b013e31812503e1.
Munoz et al., A novel p38α MAPK inhibitor suppresses brain proinflammatory cytokine up-regulation and attenuates synaapic dysfunction and behavioral deficits in an Alzheimer's disease mouse model. Jour Neuroinflamm. 2007; 4(21): 1-14.
Munoz et al., Targeting p38 MAPK pathway for the treatment of Alzheimer's disease. Neuropharmacology. Mar. 2010;58(3):561-8. doi: 10.1016/j.neuropharm.2009.11.010. Epub Dec. 4, 2009.
Nair et al., A simple practice guide for dose conversion between animals and human. J Basic Clin Pharm. Mar. 2016;7(2):27-31. doi: 10.4103/0976-0105.177703.
Nava-Mesa et al., GABAergic neurotransmission and new strategies of neuromodulation to compensate synaptic dysfunction in early stages of Alzheimer's disease. Front Cell Neurosci. Jun. 25, 2014;8:167. doi: 10.3389/fncel.2014.00167. eCollection 2014.
Neef et al., Dementia with Lewy bodies: an emerging disease. Am Fam Physician. Apr. 1, 2006;73(7):1223-9.
Nixon, Endosome function and dysfunction in Alzheimer's disease and other neurodegenerative diseases, Neurobiol Aging. Mar. 1, 2005;26(3):373-82.
No Author Listed, Activase (Alteplase), Highlights of Prescribing Information, Genentech, Inc., 16 pages (2015).
No Author Listed, Cognitive Effects of Oral p38 Alpha Kinase Inhibitor Neflamapimod in Dementia with LewyBodies (AscenD-LB). ClinicalTrials.gov. Jun. 28, 2019. https:J/clinicaltrials.gov/ct2/show/NCT04001517. retrieved on Sep. 25, 2020.
No Author Listed, EIP Pharma Announces Positive Phase 2 Results for Neflamapimod in Mild-to-Moderate Dementia with Lewy bodies (DLB). EIP Pharma Inc. Oct. 6, 2020. 3 pages.
No Author Listed, Proof-of-Concept Study of a Ssledive p38 MAPK Alpha Inhibitor, Netlamapimod, in Subfects with Mild Alzheimer's Disease (Reverse-SD). Clinical Trials. Identifier NCT03402659. 20 pages. Last updated: Oct. 27, 2021. Last accessed: Jan. 6, 2023. https://clinicaltrials.gov/ct2/show/results/NCTO3402659?view=results.
No Author Listed, The Difference Between Lewy Body Dementia, Parkinson's Disease and Alzheimer's Disease. Davis Phinney Foundation. Mar. 8, 2018. 23 pages. https://davisphinneyfoundation.org/difference-lewy-body-dementia-parkinsons-diseasealzheimers-disease/ [last accessed Nov. 4, 2021].
O'Callaghan et al., Beyond and below the cortex: the contribution of striatal dysfunction to cognition and behaviour in neurodegeneration. J Neurol Neurosurg Psychiatry. Apr. 2014;85(4):371-8. doi: 10.1136/jnnp-2012-304558. Epub Jul. 6, 2013.
Paik et al., Role of GABA plasticity in stroke recovery. Neural Regen Res. Dec. 1, 2014;9(23):2026-8. doi: 10.4103/1673-5374.147920.
Palmqvist et al., Prediction of future Alzheimer's disease dementia using plasma phospho-tau combined with other accessible measures. Nat Med. Jun. 2021;27(6): 10341042. doi: 10.1038/s41591-021-01348-z. Epub May 24, 2021.
Paoletti et al., The Challenge of Disease-Modifying Therapies in Parkinson's Disease: Role of CSF Biomarkers. Biomolecules. Feb. 19, 2020;10(2):335. doi: 10.3390/biom10020335.
Paul, Promising New Alzheimer's 'Drug' Halts Memory Loss, 'Drug' strikes newly identified target and could be used early in disease. Northwestern University News, 3 pages (2013) Online, last accessed Apr. 23, 2015 <http://www.northwestern.edu/newscenter/stories/2013/06/promising-new-alzheimers-drug-halts-memory-loss.html>.
Pensalfini et al., Endosomal Dysfunction Induced by Directly Overactivating Rab5 Recapitulates Prodromal and Neurodegenerative Features of Alzheimer's Disease. Cell Rep. Nov. 24, 2020;33(8):108420. doi: 10.1016/j.celrep.2020.108420.
Piao et al., Administration of the p38 MAPK inhibitor SB203580 affords brain protection with a wide therapeutic window against focal ischemic insult. J. Neurosci. Res. 2003; 73(4):537-44.
Pinsetta et al., Rational Design of Novel Potential p38x MAPK Inhibitors with Drug-like Properties Using Pharmacophore and Similarity-based Virtual Screening Procedures. Current Bioactive Compounds. 2013; 9(1): 3-13.
Power et al., Lewy Bodies and the Mechanisms of Neuronal Cell Death in Parkinson's Disease and Dementia with Lewy Bodies. Brain Pathol. Jan. 2017;27(1):3-12. doi: 10.1111/bpa.12344. Epub Jan. 18, 2016.
Qingwei et al., Cognitive frailty, a novel target for the prevention of elderly dependency. Ageing Res Rev. Mar. 2015;20:1-10. doi: 10.1016/j.arr.2014.12.004. Epub Dec. 30, 2014.
Rahimi et al., Prevalence of mixed pathologies in the aging brain. Alzheimers Res Ther. Nov. 21, 2014;6(9):82. doi: 10.1186/s13195-014-0082-1. eCollection 2014.
Reagan-Shaw et al., Dose translation from animal to human studies revisited. Faseb J. Mar. 2008;22(3):659-61. doi: 10.1096/fj.07-9574LSF. Epub Oct. 17, 2007.
Regan et al., Pyrazole Urea-Based Inhibitors of p38 MAP Kinase: From Lead Compound to Clinical Candidate. J Med Chem. Jul. 4, 2002;45(14):2994-3008. doi: 10.1021/jm020057r.
Richards et al., Neurodegenerative diseases have genetic hallmarks of autoinflammatory disease. Hum Mol Genet. Aug. 1, 2018;27(R2):R108-R118. doi: 10.1093/hmg/ddy139.
Roh et al., Stealth attack: plaque-specific antibody allows for efficient AB removal without side effects. Neuron. Dec. 6, 2012;76(5):859-61. doi: 10.1016/j.neuron.2012.11.018.
Rojas et al., Functional assessment of four types of disintegrants and their effect on the spironolactone release properties. AAPS PharmSciTech. Dec. 2012;13(4):1054-62. doi: 10.1208/s12249-012-9835-y. Epub Aug. 17, 2012.
Roy et al., Targeting human central nervous system protein kinases: An isoform selective p38αMAPK inhibitor that attenuates disease progression in Alzheimer's disease mouse models. ACS Chem Neurosci. Apr. 15, 2015;6(4):666-80. doi: 10.1021/acschemneuro.5b00002. Epub Feb. 23, 2015.
Scheltens et al., Quantitative PET Study of the Effect of the p38a Kinase Inhibitor VX-745 on Brain Amyloid Plaque Load in Patients with Early Alzheimer's Disease. J Prev Alz Dis. Dec. 2016;3:272.
Schnöder et al., Deficiency of Neuronal p38α-MAPK Attenuates Amyloid Pathology in Alzheimer's Mouse and Cell Models through Facilitating Lysosomal Degradation of BACE1. J Biol Chem. Jan. 29, 2016;291(5):2067-79. doi: 10.1074/jbc.M115.695916. Epub Dec. 9, 2015.

(56) References Cited

OTHER PUBLICATIONS

Sheng, Research on Pathogenesis and Drugs of Senile Dementia. Scientific and Technical Literature Press. 2003. p. 54. ISBN 9787502344184.
Stein et al., Chapter 29. The MAP Kinase Family: New "MAPs" for Signal Transduction Pathways and Novel Targets for Drug Discovery. Ann Rep Med Chem. 1996;31:289-98. doi:10.1016/S0065-7743(08)60468-6.
Stylianou et al., Quantitative electroencephalography as a marker of cognitive fluctuations in dementia with Lewy bodies and an aid to differential diagnosis. Clin Neurophysiol. Jun. 2018;129(6):1209-1220. doi: 10.1016/j.clinph.2018.03.013. Epub Apr. 3, 2018.
Teipel et al., Predictors of cognitive decline and treatment response in a clinical trial on suspected prodromal Alzheimer's disease. Neuropharmacology. Sep. 2016;108:128-35. doi: 10.1016/j.neuropharm.2016.02.005. Epub Feb. 10, 2016.
Terry, Eip Pharma Closes $20.5 to Fund Alzheimer's Studies. May 16, 2018. https:J/Www.biospace.com/article/eip-phanna-closes-W-5-to-fund-alzheimer-s-studies. retrieved on Sep. 25, 2020.
Thomas, Are you heavier or shorter than the average American? CNN Health. Last updated: Dec. 20, 2018. www.cnn.com/2018/12/20/health/us-average-height-weight-report/index.html.
Tse et al., Targeting pre-existing plaques in AD. Nature Reviews Drug Discovery. 2013; 12:100-101.
Van Der Zande et al., EEG Characteristics of Dementia With Lewy Bodies, Alzheimer's Disease and Mixed Pathology. Front Aging Neurosci. Jul. 3, 2018;10:190. doi: 10.3389/fnagi.2018.00190. eCollection 2018.
Ventriglia et al., Serum Brain-Derived Neurotrophic Factor Levels in Different Neurological Diseases. Biomed Res Int. 2013;2013:901082. doi: 10.1155/2013/901082. Epub Aug. 19, 2013.
Verkaar et al., Inhibition of Wnt/β-catenin signaling by p38 MAP kinase inhibitors is explained by cross-reactivity with casein kinase Iδ/ϵ. Chem Biol. Apr. 22, 2011;18(4):485-94. doi: 10.1016/j.chembiol.2011.01.015.
Villemagne et al., Longitudinal assessment of Aβ and cognition in aging and Alzheimer disease. Ann Neurol. Jan. 2011;69(1):181-92. doi: 10.1002/ana.22248.
Volpicelli-Daley, Effects of α-synuclein on axonal transport. Neurobiol Dis. Sep. 2017;105:321-327. doi: 10.1016/j.nbd.2016.12.008. Epub Dec. 9, 2016.
Wadsworth et al., RWJ 67657, a Potent, Orally Active Inhibitor of p38 Mitogen-Activated Protein Kinase. J Pharmacol Exp Ther. Nov. 1999;291(2):680-7.
Wang et al., Memory deficits induced by inflammation are regulated by alpha5-subunit-containing GABAA receptors. Cell Rep. Sep. 27, 2012;2(3):488-96. doi: 10.1016/j.celrep.2012.08.022. Epub Sep. 20, 2012.
Watterson et al., Development of Novel In Vivo Chemical Probes to Address CNS Protein Kinase Involvement in Synaptic Dysfunction. PLoS One. Jun. 26, 2013;8(6):e66226. doi: 10.1371/journal.pone.0066226. Print 2013.
Weisman et al., A Double-Blind, Placebo-Controlled Trial of VX-745, an Oral p38 Mitogen Activated Protein Kinase (MAPK) Inhibitor, in Patients with Rheumatoid Arthritis (RA), Abstract FRI0018. European League Against Rheumatism (EULAR). 2002.
Weitzner et al., Morris Water Maze Test: Optimization for Mouse Strain and Testing Environment. J Vis Exp. Jun. 22, 2015;(100):e52706. doi: 10.3791/52706.
Wiesmann et al., Vascular aspects of cognitive impairment and dementia. J Cereb Blood Flow Metab. Nov. 2013;33(11):1696-706. doi: 10.1038/jcbfm.2013.159. Epub Sep. 11, 2013.
Wilson et al., Cholinergic Basal Forebrain Volumes Predict Gait Decline in Parkinson's Disease. Mov Disord. Mar. 2021;36(3):611-621. doi: 10.1002/mds.28453. Epub Dec. 31, 2020.
Wong et al., Activity-dependent BDNF release via endocytic pathways is regulated by synaptotagmin-6 and complexin. Proc Natl Acad Sci U S A. Aug. 11, 2015;112(32):E4475-84. doi: 10.1073/pnas.1511830112. Epub Jul. 27, 2015.
Wood, Could anti-amyloid-beta immunotherapy do more harm than good? Nat Rev Neurol. Jan. 2016;12(1):2. doi: 10.1038/nrneurol.2015.227. Epub Nov. 27, 2015.
Woodford et al., Cognitive assessment in the elderly: a review of clinical methods. QJM. Aug. 2007;100(8):469-84. doi: 10.1093/qjmed/hcm051. Epub Jun. 12, 2007.
Wu et al., Tonic inhibition in dentate gyrus impairs long-term potentiation and memory in an Alzheimer's disease model. Nat Commun. Jun. 13, 2014;5:4159. doi: 10.1038/ncomms5159.
Xu et al., Long-term Effects of Cholinesterase Inhibitors on Cognitive Decline and Mortality. Neurology. Apr. 27, 2021;96(17):e2220-e2230. doi: 10.1212/WNL.0000000000011832. Epub Mar. 19, 2021.
Yadav et al., Co-crystals: a novel approach to modify physicochemical properties of active pharmaceutical ingredients. Indian J Pharm Sci. 2009;71(4):359-370. doi: 10.4103/0250-474X.57283.
Yang et al., Protective Effects of p38 MAPK Inhibitor SB202190 against Hippocampal Apoptosis and Spatial Learning and Memory Deficits in a Rat Model of Vascular Dementia. Biomed Res Int. 2013;2013:215798. doi: 10.1155/2013/215798. Epub Dec. 25, 2013.
Yasuda et al., p38 MAP kinase inhibitors as potential therapeutic drugs for neural diseases. Cent. Nerv. Syst. Agents Med. Chem. 2011; 11(1):45-59.
Yiannopoulou et al., Reasons for Failed Trials of Disease-Modifying Treatments for Alzheimer Disease and Their Contribution in Recent Research. Biomedicines. Dec. 9, 2019;7(4):97. doi: 10.3390/biomedicines7040097.
Zeman et al., Diagnosis of Dementia Using Nuclear Medicine Imagining Modalities, 12 Chapters on Nuclear Medicine, pp. 199-230 (2011).
Zhu et al., CD45 Deficiency Drives Amyloid-β Peptide Oligomers and Neuronal Loss in Alzheimer's Disease Mice. J Neurosci. Jan. 26, 2011;31(4):1355-65. doi: 10.1523/JNEUROSCI.3268-10.2011.
Zhu et al., CD45RB Is a Novel Molecular Therapeutic Target to Inhibit Aβ Peptide-Induced Microglial MAPK Activation. PLoS One. May 14, 2008;3(5):e2135. doi: 10.1371/journal.pone.0002135.
Alam et al., (LP14) Impact of Alzheimer's disease (AD) related co-pathology on treatment effects of the oral p38α kinase inhibitor neflamapimod in mild-to-moderate dementia with Lewy bodies (DLB). Presented Nov. 10, 2021 at the 14th Clinical Trials in Alzheimer's Disease (CTAD) meeting. pp. S124-S125.
Loy et al., p38α and p38β mitogen-activated protein kinases determine cholinergic transdifferentiation of sympathetic neurons. J Neurosci. Aug. 24, 2011;31(34):12059-67. doi: 10.1523/JNEUROSCI.0448-11.2011.

* cited by examiner

Immediate Recall - ptau < 2.2 pg/ML
Delayed Recall - ptau < 2.2 pg/mL
Recognition - ptau < 2.2 pg/mL
Immediate Recall - ptau ≥ 2.2 pg/mL
Delayed Recall - ptau≥2.2 pg/mL
Recognition - ptau≥2.2 pg/mL Number of Words
6
4
2
0
-2
-4
-6
*
**

TREATMENT OF A SELECTIVE POPULATION OF PATIENTS HAVING DEMENTIA WITH LEWY BODIES

REFERENCE TO RELATED APPLICATIONS

This application is a continuation under 35 U.S.C. § 120 of U.S. application Ser. No. 18/707,318, filed May 3, 2024, which is a national stage filing under 35 U.S.C. 371 of International Patent Application Serial No. PCT/US2022/049052, filed Nov. 4, 2022, which claims priority under 35 U.S.C. § 119(e) to U.S. Provisional Patent Application No. 63/276,529, filed Nov. 5, 2022, each of which are hereby incorporated by reference in their entireties.

BACKGROUND

Dementia with Lewy bodies (DLB) is the second most common dementia after Alzheimer's disease and yet there are no approved therapies to address this progressive disorder.

SUMMARY

The present disclosure encompasses the discovery that administration of a selective p38 α MAPK inhibitor, neflamapimod, is effective to treatment a select patient population that has Dementia with Lewy Bodies (DLB) but no substantial tau pathology. Specifically, neflamapimod was effective to treat DLB symptoms in patients with no substantial tau pathology characterized by biomarkers of tau pathology, such as levels of phosphorylated tau (ptau) in plasma. Elevated ptau level in plasma is a surrogate measure of tau pathology in brain, which is often associated with Alzheimer's disease pathology. It has been discovered herein that a subset of DLB patients have tau pathology, while another subset of DLB patients do not have substantial tau pathology, and that patients without substantial tau pathology respond differently to neflamapimod therapy. Provided herein are methods of treatment comprising administering neflamapimod to DLB patients that do not have substantial tau pathology.

In some embodiments, provided is a method of treating Dementia with Lewy Bodies (DLB) in a subject having DLB but no substantial tau pathology, the method comprising administering a selective p38α mitogen activated protein kinase (MAPK) inhibitor to the subject.

In some embodiments, the p38α mitogen activated protein kinase (MAPK) inhibitor is neflamapimod.

In some embodiments no substantial tau pathology in a subject is characterized by level of ptau181 in plasma. In some embodiments no substantial tau pathology in a subject is characterized by level of ptau217 in plasma. In some embodiments, no substantial tau pathology in a subject is characterized by positron emission topography (PET) of brain.

In some embodiments, no substantial tau pathology in a subject is associated with a level of amyloid beta (Aβ) 42 in cerebrospinal fluid in the subject that is lower than that of subjects diagnosed as having Alzheimer's Disease.

In some embodiments, no substantial tau pathology in a subject is characterized by a level of plasma ptau lower than that of a subject having Alzheimer's Disease or Alzheimer's Disease related pathology as measured in a Simoa ptau181 assay, or equivalent thereof of another assay methodology that measures plasma ptau.

In some embodiments, no substantial tau pathology in a subject is characterized by a ptau181 level of less than 2.2 pg/mL in plasma. In some embodiments, no substantial tau pathology in a subject is characterized by a ptau181 level of less than 2.2 pg/mL in plasma assessed by Simoa platform assay, or equivalent thereof of another assay methodology.

In some embodiments, provided herein are methods of treating alpha-synuclein associated degenerative disease in a subject having DLB but no substantial tau pathology the methods comprising administering to the subject a selective p38α mitogen activated protein kinase (MAPK) inhibitor.

In some embodiments, provided herein are methods of inhibiting neuronal loss in the central nervous system in a subject having DLB but no substantial tau pathology, the methods comprising administering to the subject a selective p38α mitogen activated protein kinase (MAPK) inhibitor.

In some embodiments, provided herein are methods of reversing endosomal dysfunction in a subject having DLB but no substantial tau pathology, the methods comprising administering to the subject a selective p38α mitogen activated protein kinase (MAPK) inhibitor.

In some embodiments, the MAPK inhibitor is neflamapimod. In some embodiments, neflamapimod is administered at 40 mg TID.

In some embodiments, the subject has cholinergic neurodegeneration in the basal forebrain. In some embodiments administration of neflamapimod results in diminished symptomatic effects of cholinergic neurodegeneration in the basal forebrain of the subject.

In some embodiments, the subject has synaptic dysfunction in the medial septum, neuronal cell loss in the hippocampus, neuronal loss in the medial septum, or neuronal cell loss in the vertical limb of the nucleus of the diagonal band. In some embodiments, the neuronal cell loss in the hippocampus is in CA2-3 regions of the hippocampus.

In some embodiments, the subject has deficits in:

(a) attention, verbal fluency, episodic memory as measured by Attention Composite z-score,
(b) deficits in mobility as measured by Timed Up and Go (TUG),
(c) memory, orientation, judgment and problem solving, community affairs, home and hobbies performance, and personal care as measured by Clinical Dementia Rating Scale (CDR-SB), and/or
(d) deficits in neuropsychological activity as measured by Neuropsychological Test Battery (NTB).

In some embodiments, the subject has alpha synuclein deposits in the hippocampus.

In some embodiments, the subject does not have Alzheimer's Disease.

In some embodiments, neflamapimod is administered to a subject having DLB and a plasma ptau181 level of less than 3 pg/mL.

In some embodiments, neflamapimod is administered to a subject having DLB and a plasma ptau181 level of less than 2.5 pg/mL.

In some embodiments, neflamapimod is administered to a subject having DLB and a plasma ptau181 level of less than 2 pg/mL.

In some embodiments, neflamapimod is administered to a subject having DLB and a plasma ptau181 level of less than 1 pg/mL.

In some embodiments, the subject is also receiving a cholinesterase inhibitor.

In some embodiments the daily amount of neflamapimod administered is equivalent to a dose of 40 mg (TID).

In some embodiments, a subject administered neflamapimod is also receiving a cholinesterase inhibitor therapy. In some embodiments, a subject having a plasma ptau level of less than 2.2 pg/mL and receiving a cholinesterase therapy is administered neflamapimod at a dose of at least 40 mg TID.

DEFINITIONS

Figure 1:
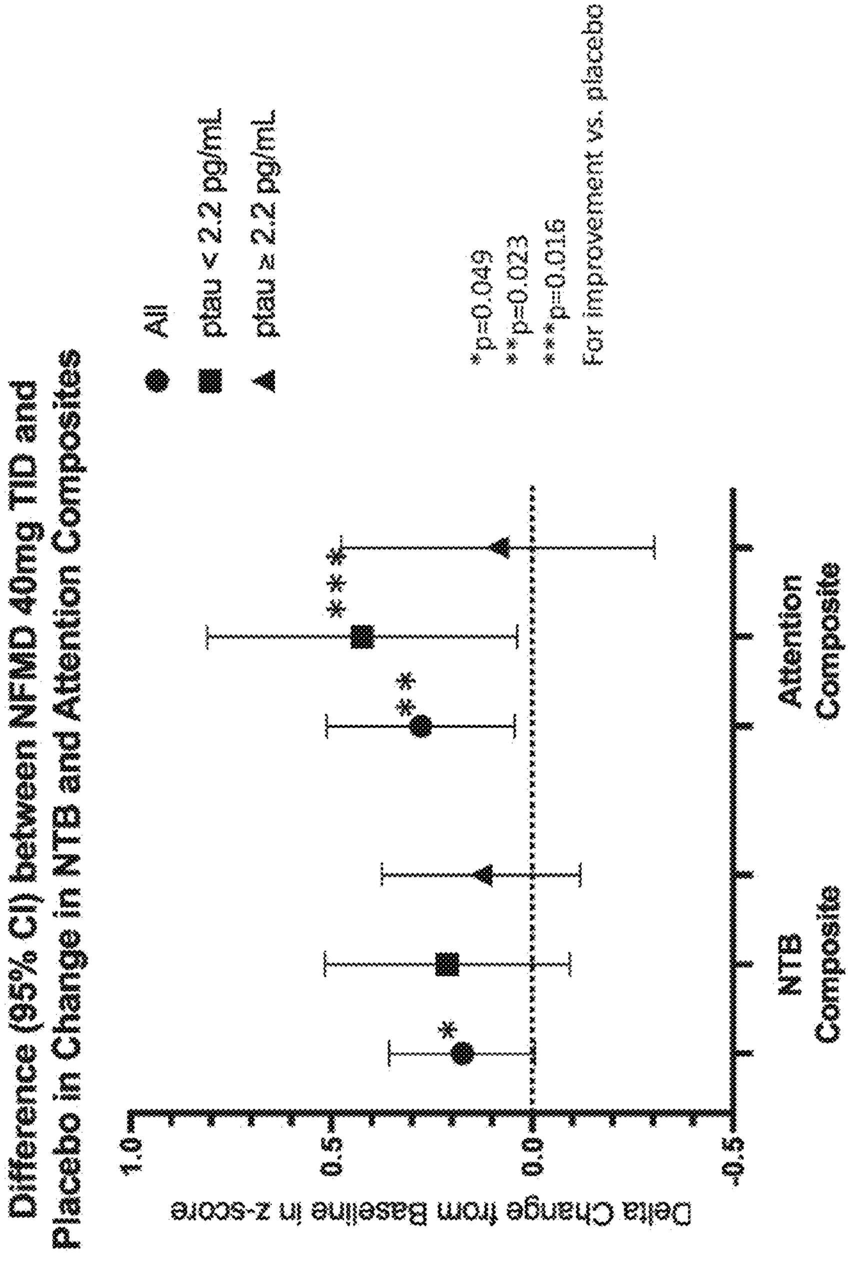
FIG. 1 shows clinical trial results in subjects receiving neflamapimod for Attention Composite z-score for tests within Neuropsychological Test Battery (NTB) that assess information processing speed. Data are presented as output (Mean, 95% CI) of analysis change from baseline utilizing Mixed Model for Repeated Measures (MMRM). Improvement is reflected as increases in NTB and Attention Composite z-scores.

Carrier: The term "carrier" refers to any chemical entity that can be incorporated into a composition containing an active agent (e.g., a p38 MAPKα inhibitor such as neflamapimod) without significantly interfering with the stability and/or activity of the agent (e.g., with a biological activity of the agent). In certain embodiments, the term "carrier" refers to a pharmaceutically acceptable carrier.

Formulation. The term "formulation" as used herein refers to a composition that includes at least one active agent (e.g., p38 MAPKα inhibitor such as neflamapimod) together with one or more carriers, excipients or other pharmaceutical additives for administration to a patient. In general, particular carriers, excipients and/or other pharmaceutical additives are selected in accordance with knowledge in the art to achieve a desired stability, release, distribution and/or activity of active agent(s) and which are appropriate for the particular route of administration.

Pharmaceutically acceptable carrier, adjuvant, or vehicle. The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Therapeutically effective amount and effective amount. As used herein, and unless otherwise specified, the terms "therapeutically effective amount" and "effective amount" of an agent refer to an amount sufficient to provide a therapeutic benefit in the treatment, prevention and/or management of a disease, disorder, or condition, e.g., to delay onset of or minimize (e.g., reduce the incidence and/or magnitude of) one or more symptoms associated with the disease, disorder or condition to be treated. In some embodiments, a composition may be said to contain a "therapeutically effective amount" of an agent if it contains an amount that is effective when administered as a single dose within the context of a therapeutic regimen. In some embodiments, a composition may be said to contain a "therapeutically effective amount" of an agent if it contains an amount that is effective when administered as more than one dose (e.g., two doses, three doses, or four or more doses) within the context of a therapeutic regimen. In some embodiments, a therapeutically effective amount is an amount that, when administered as part of a dosing regimen, is statistically likely to delay onset of or minimize (reduce the incidence and/or magnitude of) one or more symptoms or side effects of a disease, disorder or condition.

Treat or Treating. The terms "treat" or "treating," as used herein, refer to partially or completely alleviating, inhibiting, delaying onset of, reducing the incidence of, yielding prophylaxis of, ameliorating and/or relieving or reversing a disorder, disease, or condition, or one or more symptoms or manifestations of the disorder, disease or condition.

Unit Dose. The expression "unit dose" as used herein refers to a physically discrete unit of a formulation appropriate for a subject to be treated (e.g., for a single dose); each unit containing a predetermined quantity of an active agent selected to produce a desired therapeutic effect when administered according to a therapeutic regimen (it being understood that multiple doses may be required to achieve a desired or optimum effect), optionally together with a pharmaceutically acceptable carrier, which may be provided in a predetermined amount. The unit dose may be, for example, a volume of liquid (e.g., an acceptable carrier) containing a predetermined quantity of one or more therapeutic agents, a predetermined amount of one or more therapeutic agents in solid form (e.g., a tablet or capsule), a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present invention will be decided by the attending physician within the scope of sound medical judgment. The specific effective dose level for any particular subject may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. In some embodiments, a unit dose of a p38 MAPKα inhibitor, such as neflamapimod is about 1 mg, 3 mg, 5 mg, 10 mg, 15 mg, 20 mg, 25 mg, 30 mg, 35 mg, 40 mg, 45 mg, 50 mg, 100 mg, 125 mg, or 250 mg.

DETAILED DESCRIPTION OF CERTAIN EMBODIMENTS

The present invention provides, among other things, compositions and methods for treating subjects that have Dementia with Lewy Bodies (DLB) and associated pathology, but no substantial tau pathology, by administering a composition comprising a selective p38 MAPKα inhibitor, such as neflamapimod. Tau pathology may be characterized by measurement of circulating (e.g., blood or plasma) levels of phospho-tau (ptau).

In some embodiments, a plasma ptau181 level of less than 2.2 pg/mL is indicative of no substantial tau pathology, and a plasma ptau181 level of equal to or greater than 2.2 pg/mL is indicative of the presence of tau pathology in brain.

In some embodiments, tau pathology in a subject is characterized by level of ptau217 in plasma, positron emission topography (PET) in brain, and/or level of amyloid beta (Aβ) 42 in cerebrospinal fluid.

Accordingly, in some embodiments, provided herein is a method of treating DLB in a subject that does not have substantial tau pathology (or Alzheimer's Disease-like pathology). In some embodiments, ptau that is measured to determine tau pathology is ptau181. In some embodiments, ptau that is measured to determine tau pathology is ptau217. In some embodiments, ptau that is measured to determine tau pathology is ptau231. See e.g., Bayoumi et al., *Alzheimer's Research & Therapy,* 13:198 (2021) for exemplary ptau assays and comparative results.

Methods of identifying or diagnosing AD-like pathology are known. For example, AD pathology can be determined by measuring a level of beta-amyloid, precursor, or fragment thereof in a subject's blood, plasma, CSF, or brain.

In some embodiments, plasma ptau181 is used as a marker of tau pathology and the threshold value for determining whether a subject has tau pathology is 2.2 pg/mL. In some embodiments, the threshold value for ptau181 is at least 1.5 pg/mL. In some embodiments, the threshold value for ptau181 is at least 1 pg/mL, 1.6 pg/mL, 1.7 pg/mL, 1.8 pg/mL, 1.9 pg/mL, 2 pg/mL, 2.1 pg/mL, 2.2 pg/mL, 2.3 pg/mL, 2.4 pg/mL, 2.5 pg/mL, 2.6 pg/mL, 2.7 pg/mL, 2.8 pg/mL, 2.9 pg/mL, or 3 pg/mL or more.

In some embodiments, the invention provides compositions and methods for treating subjects susceptible or at risk of development or progression of DLB.

Various aspects of the invention are described in detail in the following sections. The use of sections is not meant to limit the invention. Each section can apply to any aspect of the invention. In this application, the use of "or" means "and/or" unless stated otherwise.

Dementia With Lewy Bodies

There is currently no therapy available for DLB that reverses and/or slows disease progression. A therapeutic intervention such as neflamapimod, that targets synaptic dysfunction, has the potential to both reverse existing synaptic deficits and slow further decline.

The central feature of DLB is a progressive dementia, i.e. decline in cognition associated with functional deficits, that is characterized by deficits in attention and executive function but can include memory deficits. In addition, associated symptoms include fluctuation in attentiveness, slowness of movement, rigidity, REM sleep disruption, visual hallucinations, anosmia, fluctuation in attentiveness, depression, apathy, and autonomic nervous system dysregulation. DLB is associate with deposits of alpha-synuclein in cells, known as Lewy bodies or Lewy neurites.

The medial septum (also known as Ch1) and the vertical limb of the diagonal band (also known as Ch2) provide cholinergic innervation to the hippocampus. Loss of neurons in the medial septum nucleus and vertical limb of the diagonal band is a specific feature of DLB that differentiates it from AD (Fujishiro et al., Acta Neuropathol, 111:109-1114 (2006). It has been discovered herein that loss of cholinergic neurons in the medial septum can be inhibited by administration of a selective p38 α MAPK inhibitor, neflamapimod.

Neflamapimod

Many extracellular stimuli, including pro-inflammatory cytokines and other inflammatory mediators, elicit specific cellular responses through the activation of mitogen-activated protein kinase (MAPK) signaling pathways. MAPKs are proline-targeted serine-threonine kinases that transduce environmental stimuli to the nucleus. Once activated, MAPKs activate other kinases or nuclear proteins through phosphorylation, including potential transcription factors and substrates. The four isoforms (α, β, δ, and γ) of p38 MAP kinase comprise one specific family of MAPKs that mediate responses to cellular stresses and inflammatory signals. Neflamapimod is a selective small-molecule inhibitor of the alpha isoform of p38 MAPK. Neflamapimod, also known as VX-745, has a chemical name of 5-(2,6-dichlorophenyl)-2-(2,4-difluorophenylthio)-6H-pyrimido [1,6-b] pyridazin-6-one

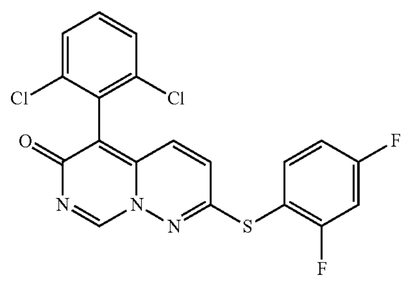

Neflamapimod (VX-745)

Pharmaceutical Compositions

In some embodiments, a provided method comprises administering to a patient a pharmaceutical composition comprising neflamapimod together with one or more therapeutic agents and a pharmaceutically acceptable carrier, adjuvant, or vehicle. In some embodiments, a pharmaceutical composition is provided comprising a dose of neflamapimod together with one or more therapeutic agents and a pharmaceutically acceptable carrier, adjuvant, or vehicle, wherein the dose of neflamapimod results in an average blood concentration of from about 1 ng/mL to about 15 ng/ml, from about 1 ng/ml to about 10 ng/mL, from about 5 ng/mL to about 15 ng/ml, or from about 5 ng/ml to about 10 ng/ml. In some embodiments, the dose of neflamapimod results in an average blood concentration of 8 ng/ml. Table 2 of WO 2017/185073 illustrates neflamapimod plasma concentration values by post-dose collection time interval, and is incorporated by reference herein.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Dosing

In some embodiments, a composition is administered in a therapeutically effective amount and/or according to a dosing regimen that is correlated with a particular desired outcome (e.g., with treating or reducing risk for disease).

In some embodiments, provided compositions are administered in a therapeutically effective amount and/or according to a dosing regimen that is correlated with a particular desired outcome (e.g., reduction in symptoms, etc.).

Alternatively or additionally, in some embodiments, an appropriate dose or amount is determined through use of one or more in vitro or in vivo assays to help identify desirable or optimal dosage ranges or amounts to be administered.

In various embodiments, provided compositions are administered at a therapeutically effective amount. Generally, a therapeutically effective amount is sufficient to achieve a meaningful benefit to the subject (e.g., treating, modulating, curing, preventing and/or ameliorating the underlying disease or condition). In some embodiments, methods of treating a subject having DLB comprise administering a therapeutically effective amount of a selective p38α inhibitor. In some embodiments, methods of treating a subject having DLB comprise administering a therapeutically effective amount of neflamapimod.

In some embodiments, a composition is provided as a pharmaceutical formulation. In some embodiments, a pharmaceutical formulation is or comprises a unit dose amount for administration in accordance with a dosing regimen correlated with achievement of disease reduction in symptoms of DLB, arrest or decrease in rate of decline of function due to DLB.

In some embodiments, a formulation comprising provided compositions as described herein is administered as a single dose. In some embodiments, a formulation comprising provided compositions as described herein is administered as two doses. In some embodiments, a formulation comprising provided compositions as described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising provided compositions as described herein is administered twice weekly, thrice weekly, every other day, daily, twice daily, or every eight hours.

In some embodiments, a formulation comprising provided compositions as described herein is administered once daily. In some embodiments, a formulation comprising provided compositions as described herein is administered twice daily. In some embodiments, the twice daily administering occurs from about 9 to 15 hours apart. In some embodiments the twice daily administering occurs about 12 hours apart. In some embodiments, a formulation comprising from about 40 mg to about 250 mg of neflamapimod is administered twice daily. In some embodiments, a formulation comprising compositions as described herein is administered three times daily. In some embodiments, the administering occurs when the patient is in a fed state. In some embodiments, the administering occurs within 30 to 60 minutes after the subject has consumed food. In some embodiments, the administering occurs when the patient is in a fasted state. The administration interval for a single individual need not be a fixed interval, but can be varied over time, depending on the needs of the individual.

In some embodiments, a formulation comprising provided compositions as described herein is administered at regular intervals. In some embodiments, a formulation comprising provided compositions as described herein is administered at regular intervals for a defined period. In some embodiments, a formulation comprising provided compositions as described herein is administered at regular intervals for 2 years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day. In some embodiments, a formulation comprising provided compositions as described herein is administered at regular intervals for 16 weeks.

EXEMPLIFICATION

The following examples are provided for illustrative purposes and are not intended to limit the scope of the invention.

Example 1

This example demonstrates that neflamapimod is particularly efficacious for treatment of subjects that have DLB without substantial tau pathology.

Treatment effects of neflamapimod in a mid-to-moderate DLB patient population receiving cholinesterase inhibitor therapy was evaluated in a 91-patient, 16-week placebo-controlled phase 2 study ("AscenD-LB Study") in mild-to-moderate DLB, neflamapimod demonstrated significant improvement, relative to placebo, in cognition (assessed by DLB specific Neuropsychological Test Battery (NTB), motor function (assessed by the Timed-Up-and-Go (TUG) Test), and cognition and function (assessed by Clinical Dementia Rating Scale sum-of-boxes (CDR-SB)).

Up to half of patients with DLB have tau pathology, or "AD copathology" (van der Lee et al, 2021) and such co-pathology may impact response to cholinesterase inhibitors (Graff-Radford et al, 2012). In patients with DLB, plasma phospho-tau (either ptau217 or ptau181) correlates with tau-PET signal in the temporal cortex and predicts abnormal tau-PET status and CSF β-amyloid status (Hall et al, 2021). Accordingly, plasma ptau181 levels were assessed in plasma samples obtained during the screening phase of AscenD-LB. The results on the association of tau pathology to treatment outcome in AscenD-LB are described below.

Dosing Regimen

With the objective of uniformly achieving a target average plasma drug concentration of 20 nM patients, dosing regimen after randomization to neflamapimod or placebo was based on weight:

Weight<80 kg: 40 mg neflamapimod capsule or matching placebo capsule BID

Weight≥80 kg: 40 mg neflamapimod capsule or matching placebo capsule TID

However, in the study, 40 mg TID achieved target plasma drug concentration; but 40 mg BID did not, missing by approximately 30-40%.

Trough plasma drug concentrations 50% lower with 40 mg BID vs. 40 mg TID

As a result, efficacy analyses compared: (1) all neflamapimod (i.e., including 40 mg BID and 40 mg TID) vs. placebo; (2) 40 mg TID (dose group that achieved target concentration) vs. placebo; and (3) 40 mg TID vs. placebo TID.

To evaluate treatment effects, linear mixed effects model for repeated measures (LMMRM) was utilized to compare outcomes in NFMD40 mg TID, the dose group that achieved therapeutic plasma drug levels and demonstrated efficacy in the main analyses reported previously, to (1) all placebo recipients, and (2) the matched higher weight placebo-recipients (placebo TID). Plasma ptau181 levels were determined by SIMOA pTau181 Assay (Quanterix) at the VU Medical Center, where the in-house defined cut-off for tau pathology was set at 2.2 pg/mL.

Baseline Disease Characteristics

At baseline, 22 of 41 (53%) of placebo and 22 of 42 (54%) of neflamapimod participants in the efficacy analysis population (baseline and on-treatment data on at least one efficacy endpoint) had plasma ptau181<2.2 pg/mL (i.e., those predicted to not have tau pathology). See Table 1.

TABLE 1

Baseline characteristics by plasma ptau181 status

| | Baseline plasma ptau181 < 2.2 pg/mL | | | Baseline plasma ptau181 ≥ 2.2 pg/mL | | |
|---|---|---|---|---|---|---|
| | Placebo (N = 23) | NFMD (N = 22) | All (N = 45) | Placebo (N = 20) | NFMD (N = 20) | All (N = 40) |
| Age (yrs) | 70.7 (6.0) | 72.6 (6.8) | 71.7 (6.4) | 73.8 (7.5) | 74.1 (6.7) | 73.9 (7.0) |
| Male | 87% | 82% | 84% | 85% | 85% | 85% |
| CDR Sum of Boxes | 4.3 (2.0) | 4.7 (2.1) | 4.5 (2.1) | 6.1 (3.4) | 5.1 (2.1) | 5.5 (2.8) |
| MMSE | 24 (3.8) | 24 (3.0) | 24 (3.4) | 23 (3.6) | 22 (3.7) | 22 (3.6) |
| ISLT (Immediate) | 15 (6.0) | 15 (6.2) | 15 (6.0) | 13 (4.6) | 12 (5.5) | 13 (5.0) |
| ISLT (Delayed) | 5 (2.3) | 4 (2.8) | 4 (2.5) | 4 (1.8) | 4 (2.8) | 4 (2.4) |
| ISLT (Recognition) | 10.7 (1.3) | 10.1 (1.6) | 10.4 (1.4) | 9.5 (2.0) | 10.8 (1.2) | 10.1 (1.8) |
| Timed Up and Go (seconds) | 14 (7.7) | 12 (3.8) | 13 (6.1) | 13 (3.6) | 14 (4.5) | 13 (4.1) |
| Fluctuating cognition | 56% | 54% | 53% | 60% | 70% | 65% |
| Visual hallucinations | 65% | 50% | 58% | 45% | 70% | 58% |
| REM sleep disorder | 83% | 59% | 71% | 65% | 55% | 60% |
| Parkinsonism | 87% | 73% | 80% | 85% | 80% | 83% |
| ≥2 core clinical features* | 91% | 73% | 82% | 85% | 90% | 88% |

*Fluctuating cognition, visual hallucinations, REM sleep disorder, or parkinsonism Mean (SD), except when shown as percentage Note:

For ISLT (delayed) and ISLT (recognition), missing data in 1 NFMD participant with baseline ptau < 2.2 pg/mL and 1 placebo participant with ptau > 2.2 pg/mL. Also missing TUG data in 1 participant with baseline ptau181 ≥ 2.2 pg/mL.

Results

For all four endpoints that had shown significant treatment effects in the main analysis (NTB z-sore, attention z-score, TUG, CDR-SB), descriptive evaluation of the results by baseline ptau181 status revealed that positive treatment effects were to the patients who were below the threshold (2.2 pg/mL) for having tan pathology, with no discernible treatment effect (positive or negative) with baseline plasma ptau181 levels above the threshold, i.e., those with tau pathology.

When LMMRM analysis was confined to patients who had ptau181<2.2 pg/mL at baseline, for both comparisons significant positive treatment favoring NFMD 40 mg TID were seen for the attention composite z-score (p=0.021 vs. placebo, difference=0.42 95% CI: 0.07, 0.78; p=0.034 vs. placebo TID, difference=0.46 z-score, 95% CI: 0.04, 0.88). Sec FIG. 1.

Figures 2A, 2B:
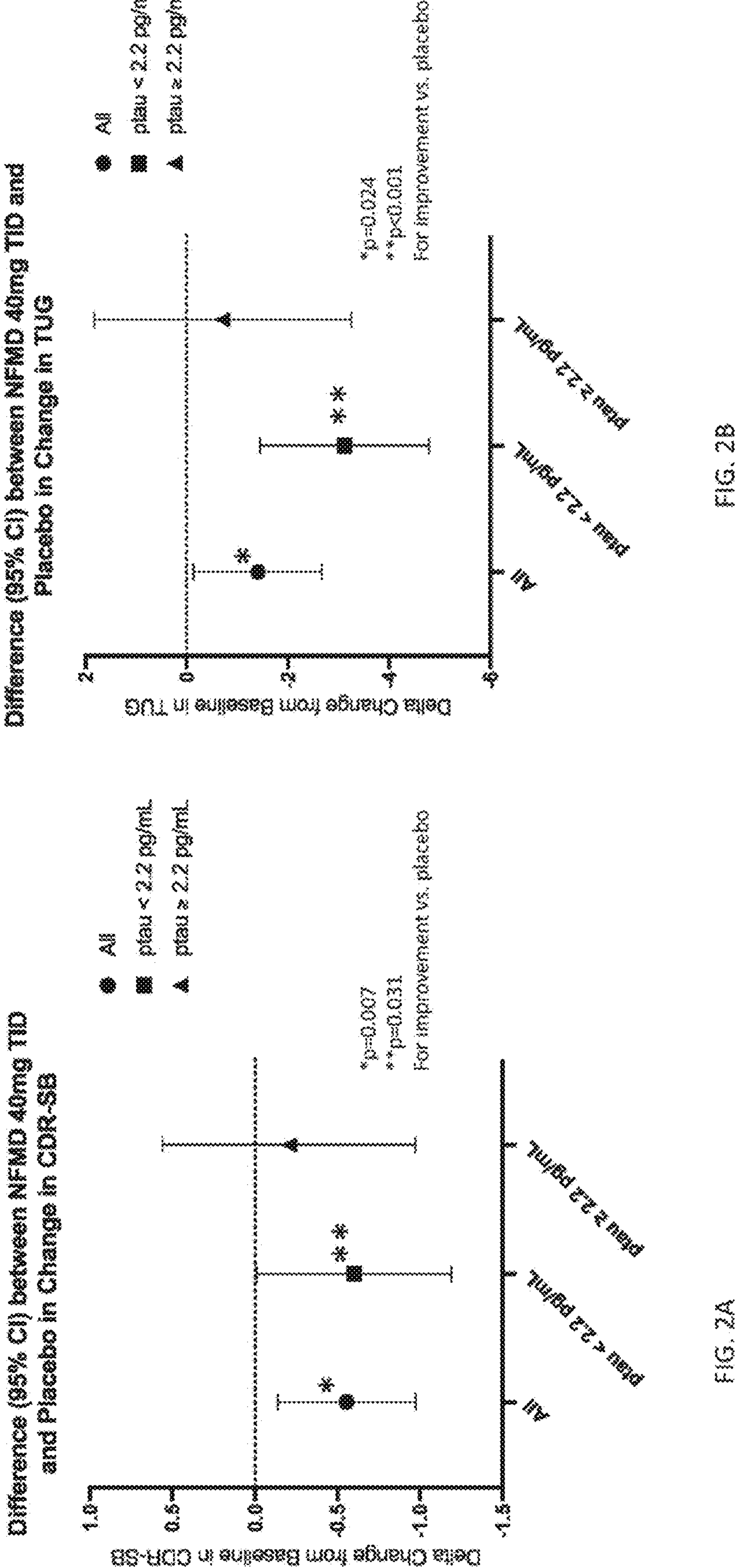
FIG. 2A shows clinical trial results in subjects receiving neflamapimod for Clinical Dementia Rating Scale (CDR-SB). Data are presented as output (Mean, 95% CI) of analysis change from baseline utilizing Mixed Model for Repeated Measures (MMRM). Improvement is reflected as a decrease in CDR-SB score. 40 mg TID vs. placebo are plotted.
FIG. 2B shows clinical trial results in subjects receiving neflamapimod for Timed Up and Go (TUG) testing. Data are presented as output (Mean, 95% CI) of analysis change from baseline utilizing Mixed Model for Repeated Measures (MMRM). Improvement is reflected as a decrease in time to complete the TUG test. 40 mg TID vs. placebo are plotted.

When LMMRM analysis was confined to patients who had ptau181<2.2 pg/mL at baseline, for both comparisons significant positive treatment favoring NFMD 40 mg TID were seen for the TUG (p<0.001 vs. placebo, difference=−3.1, 95% CI: −4.7, −1.6; p=0.010 vs. placebo TID, difference=−3.5 seconds, 95% CI: −6.1, −0.9). See FIG. 2B.

When LMMRM analysis was confined to patients who had ptau181<2.2 pg/mL at baseline, for both comparisons significant positive treatment favoring NFMD 40 mg TID were seen for the CDR-SB (p=0.031 vs. placebo, difference=−0.60, 95% CI: −1.14, −0.06; p=0.009 vs. placebo TID, difference=−0.93 points, 95% CI: −1.61, −0.25). See FIG. 2A.

When LMMRM analysis was confined to patients who had ptau181<2.2 pg/mL at baseline, for both comparisons significant positive treatment favoring NFMD 40 mg TID were seen for the NTB z-score, though numerically favoring NFMD 40 mg TID treatment (difference=0.21 vs. placebo, 95% CI: −0.07, 0.49; difference=0.25 vs. placebo TID, 95% CI: −0.07, 0.57), with the limited sample size the differences were not significant (p=0.13 vs. placebo, p=0.12 vs. placebo TID). However, for the NTB, a significant PK-PD relationship (p=0.035, r=0.46, for estimated trough plasma neflamapimod drug concentration vs. NTB z-score score) was evident.

Figure 3:
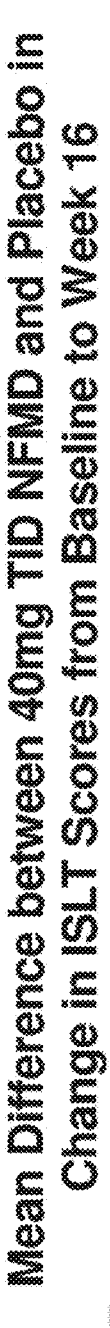
FIG. 3 shows clinical trial results in subjects receiving neflamapimod for the International Shopping List Test (ISLT). Data are presented as output (Mean, 95% CI) of analysis change from baseline utilizing Mixed Model for Repeated Measures (MMRM). Improvement is reflected by an increase in ISLT score.
Figure 3:
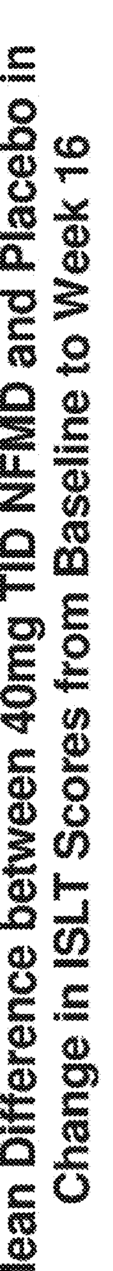
Figure 3:
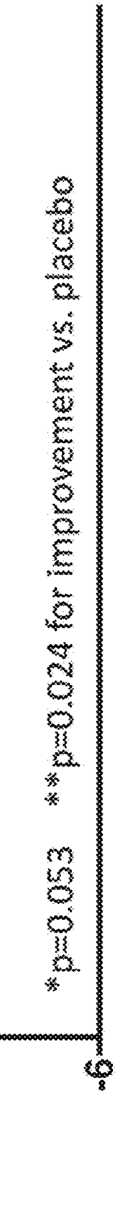

When LMMRM analysis was confined to patients who had ptau181<2.2 pg/mL at baseline, for both comparisons, significant positive trends favoring NFMD 40 mg TID were seen for ISLD immediate recall (p=0.053 vs. placebo, difference=2.1 words 95% CI: −0.0, 4.2; p=0.063 vs. placebo TID, difference=2.3 words, 95% CI: −0.1, 4.7) and significant positive improvement favoring NFMD 40 mg TID for ISLD recognition (p=0.024 vs. placebo, difference=1.4 words, 95% CI: 0.2, 2.5; p=0.035 vs. placebo TID, difference=0.9 words, 95% CI: 0.1, 1.7). See FIG. 3. The positive effect on ISLD recognition is consistent with an effect on working memory.

Efficacy analyses of the major endpoints show that the response in the patients with baseline plasma ptau181<2.2 pg/mL (i.e., those without substantial tau pathology) appears to be better than the response in patients with baseline plasma ptau181 levels ≥2.2 pg/mL (i.e., those with tau pathology in brain, and potentially mixed AD-related pathology).

When the protocol-specified efficacy analysis (mixed model for repeated measures) is confined to patients without substantial tau pathology, the magnitude of the neflamapimod treatment effect relative to placebo is substantial and clinically important. See Table 2.

TABLE 2

Summary of neflamapimod efficacy in DLB patient populations without tau pathology (baseline plasma ptau181 < 2.2 pg/mL)

| | Improvement in all neflamapimod vs. placebo | | Improvement in neflamapimod 40 mg TID vs. placebo | | Improvement in neflamapimod 40 mg TID vs. placebo TID | |
|---|---|---|---|---|---|---|
| Cognition: | p-value | Effect size | p-value | Effect size | p-value | Effect Size |
| NTB* | >0.2 | 0.15 | 0.133 | 0.56 | 0.123 | 0.61 |
| Attention | 0.185 | 0.29 | 0.021 | 0.78 | 0.034 | 0.70 |
| Timed up and Go | 0.024 | 0.40 | <0.001 | 0.74 | 0.010 | 0.70 |
| CDR-SB | 0.129 | 0.58 | 0.031 | 0.70 | 0.009 | 0.98 |

Compared to the results in the overall population, the magnitude of the neflamapimod treatment effect relative to placebo for the individual endpoints was 1.5 to 2.0-fold greater in the population with plasma ptau181<2.2 pg/mL at baseline.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A method for treating a subject having Dementia with Lewy Bodies (DLB) but no substantial tau pathology, the method comprising administering neflamapimod to the subject.

2. The method of claim 1, wherein no substantial tau pathology in a subject is characterized by level of ptau181 in plasma.

3. The method of claim 1, wherein no substantial tau pathology in a subject is characterized by level of ptau217 in plasma.

4. The method of claim 1, wherein no substantial tau pathology in a subject is characterized by positron emission topography (PET) of brain.

5. The method of claim 1, wherein no substantial tau pathology in a subject is associated with a level of amyloid beta (Aβ) 42 in cerebrospinal fluid in the subject that is lower than that of subjects diagnosed as having Alzheimer's Disease.

6. The method of claim 4, wherein no substantial tau pathology in a subject is characterized by a level of plasma ptau lower than that of a subject having Alzheimer's Disease or Alzheimer's Disease related pathology as measured in a Simoa ptau 181 assay.

7. A method of inhibiting neuronal loss in the central nervous system in a subject having DLB but no substantial tau pathology, the method comprising administering to the subject neflamapimod.

8. A method of reversing endosomal dysfunction in a subject having DLB but no substantial tau pathology, the method comprising administering to the subject neflamapimod.

9. The method of claim 8, wherein the neflamapimod is administered at 40 mg TID.

10. The method of claim 1, wherein the subject has cholinergic neurodegeneration in the basal forebrain.

11. The method of claim 10, wherein the administration results in diminished symptomatic effects of cholinergic neurodegeneration in the basal forebrain of the subject.

12. The method of claim 1, wherein the subject has synaptic dysfunction in the medial septum, neuronal cell loss in the hippocampus, neuronal loss in the medial septum, or neuronal cell loss in the vertical limb of the nucleus of the diagonal band.

13. The method of claim 12, wherein the neuronal cell loss in the hippocampus is in CA2-3 regions of the hippocampus.

14. The method of claim 1, wherein the subject has deficits in:

(a) attention, verbal fluency, episodic memory as measured by Attention Composite z-score, (b) deficits in mobility as measured by Timed Up and Go (TUG), (c) memory, orientation, judgment and problem solving, community affairs, home and hobbies performance, and personal care as measured by Clinical Dementia Rating Scale (CDR-SB), and/or (d) deficits in neuropsychological activity as measured by Neuropsychological Test Battery (NTB).

15. The method of claim 1, wherein the subject has alpha synuclein deposits in the hippocampus.

16. The method of claim 1, wherein the subject does not have Alzheimer's Disease.

* * * * *